United States Patent [19]  [11] Patent Number: 4,977,287
Kakimoto et al.  [45] Date of Patent: Dec. 11, 1990

[54] ORGANOGERMANIUM COMPOUNDS AND PROCESS FOR PRODUCING THE SAME

[75] Inventors: Norihiro Kakimoto, Machida; Kunie Nakamura, Sagamihara; Toru Yoshihara, Tama, all of Japan

[73] Assignee: Asai Germanium Research Institute Co., Tokyo, Japan

[21] Appl. No.: 400,062

[22] Filed: Aug. 29, 1989

[30] Foreign Application Priority Data

Aug. 29, 1988 [JP] Japan ................ 63-213899

[51] Int. Cl.$^5$ ............................................. C07F 7/30
[52] U.S. Cl. ........................ 556/83; 556/88; 556/89
[58] Field of Search ............ 556/83, 87, 88, 89; 514/492

[56] References Cited

U.S. PATENT DOCUMENTS

| | | | |
|---|---|---|---|
| 3,793,455 | 2/1974 | Asai et al. | 514/492 |
| 4,361,579 | 11/1982 | Munakata et al. | 556/89 X |
| 4,501,702 | 2/1985 | Bulten et al. | 556/83 |
| 4,681,960 | 7/1987 | Kakimoto et al. | 556/83 |
| 4,720,564 | 1/1988 | Kakimoto et al. | 556/83 |
| 4,772,628 | 9/1988 | Kakimoto et al. | 514/492 |

FOREIGN PATENT DOCUMENTS 1550227 8/1979 United Kingdom .

*Primary Examiner*—Arthur C. Prescott
*Attorney, Agent, or Firm*—Oblon, Spivak, McClelland, Maier & Neustadt

[57] ABSTRACT

The present invention provides (A) an organogermanium compound represented by the general formula (1)

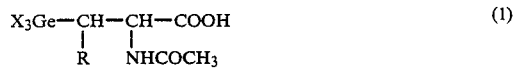

wherein X is a halogen atom and R is a hydrogen atom, a lower alkyl group or a phenyl group, or by the general formula (2)

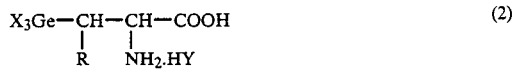

wherein X and Y are each a halogen atom and R is a hydrogen atom, a lower alkyl group or a phenyl group, or by the general formula (3-O),

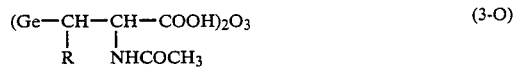

wherein R is a hydrogen atom, a lower alkyl group or a phenyl group, or by the general formula (3-S),

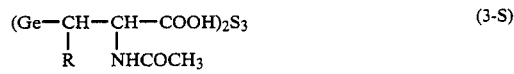

wherein R is a hydrogen atom, a lower alkyl group or a phenyl group, or by the general formula (4-O),

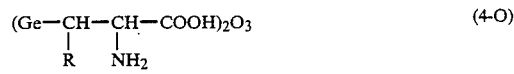

wherein R is a hydrogen atom, a lower alkyl group or a phenyl group, or by the general formula (4-S),

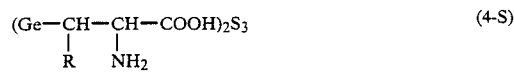

wherein R is a hydrogen atom, a lower alkyl group or a phenyl group, and (B) a process for producing an organogermanium compound represented by each of the formulas (3-O), (3-S), (4-O) and (4-S).

13 Claims, 3 Drawing Sheets

ORGANOGERMANIUM COMPOUNDS AND PROCESS FOR PRODUCING THE SAME

FIELD OF THE INVENTION

The present invention relates to organogermanium compounds and a process for producing the same.

BACKGROUND OF THE INVENTION

In recent years, study on organic compounds of germanium (a homologue of carbon) has actively been conducted, and many study results have been presented or published. Thus, attention is being paid to organogermanium compounds in various fields, particularly medical and pharmaceutical fields.

For example, it is reported that carboxyethylgermanium sesquioxide (Japanese Patent Publication No. 2498/1971) which is an organogermanium compound formed by bonding of a propionic acid derivative of germanium and oxygen atom at a 2:3 ratio shows a hypotensive action to spontaneous hypertensive rats, an amyloidosis-alleviating action, a macrophages and NK cells-augmenting action, an interferon-inducing action, an antitumor action, etc. The above sesquioxide is in trial use clinically.

The above carboxyethylgermanium sesquioxide is represented by the following basic chemical formula.

If in the above formula an amino group is introduced at the α-position of the carboxyl group —COOH to obtain a compound represented by the following chemical formula, this compound can be viewed as an amino acid.

It is well known that amino acid is a generic name for compounds represented by the following chemical formula and exists in every creature as its essential component. The importance of amino acid lies in that a plurality of amino acids bond to each other to form various proteins and further in that amino acids are metabolized in living body in various ways to become precursors for other substances which are important to living body.

Accordingly, if an amino group could be introduced, as an additional structure, into the above mentioned carboxyethylgermanium sesquioxide which is already found to have excellent pharmacological actions, the resulting organogermanium compound is highly expected to find novel utility.

PROBLEMS TO BE SOLVED BY THE INVENTION

Conventionally known derivatives of carboxyethylgermanium sesquioxide all have alkyl groups as side chains, as typified by a compound of the following basic chemical formula wherein R is a hydrogen atom or an alkyl group (Japanese Patent Publication No. 28070/1988). There has been known a derivative of carboxyethylgermanium sesquioxide having an amino group as a side chain.

U.S. Pat. No. 3,793,455 gives chemical formulas of carboxyethylgermanium sesquioxide derivatives having an amino acid structure. However, it is found that production of an organogermanium compound having an amino acid structure in accordance with the process described in the above literature is impossible. Therefore, compounds represented by the following chemical formula are provided for the first time by the present invention.

SUMMARY OF THE INVENTION

The present invention has been made in order to solve the above mentioned problems of the prior art. According to the present invention, there is provided an organogermanium compound represented by the general formula (1)

wherein X is a halogen atom and R is a hydrogen atom, a lower alkyl group or a phenyl group.

According to the present invention, there is also provided an organogermanium compound represented by the general formula (2)

wherein X and Y are each a halogen atom and R is a hydrogen atom, a lower alkyl group or a phenyl group.

According to the present invention, there is also provided an organogermanium compound represented by the general formula (3-O)

wherein R is a hydrogen atom, a lower alkyl group or a phenyl group.

According to the present invention, there is also provided an organogermanium compound represented by the general formula (3-S)

wherein R is a hydrogen atom, a lower alkyl group or a phenyl group.

According to the present invention, there is also provided an organogermanium compound represented by the general formula (4-O)

(4-O)

wherein R is a hydrogen atom, a lower alkyl group or a phenyl group.

According to the present invention, there is also provided an organogermanium compound represented by the general formula (4-S)

(4-S)

wherein R is a hydrogen atom, a lower alkyl group or a phenyl group.

According to the present invention, there is further provided a process for producing an organogermanium compound represented by the general formula (3-O)

(3-O)

(R is a hydrogen atom, a lower alkyl group or a phenyl group), which process comprises adding a halide compound represented by the general formula (6)

(6)

(X is a halogen atom) to an unsaturated compound represented by the general formula (5)

(5)

(R has the same definition as given above) to form a trihalide compound represented by the general formula (1)

(1)

(X and R each have the same definition as given above) and hydrolyzing the trihalide compound to obtain a compound represented by the general formula (3-O) shown above.

According to the present invention, there is also provided a process for producing an organogermanium compound represented by the general formula (3-S)

(3-S)

(R is a hydrogen atom, a lower alkyl group or a phenyl group),which process comprises adding a halide compound represented by the general formula (6)

(6)

(X is a halogen atom) to an unsaturated compound represented by the general formula (5)

(5)

(R has the same definition as given above) to form a trihalide compound represented by the general formula (1)

(1)

(X and R each have the same definition as given above) and reacting the trihalide compound with hydrogen sulfide to obtain a compound represented by the general formula (3-S) shown above.

According to the present invention, there is also provided a process for producing an organogermanium compound represented by the general formula (4-O)

(4-O)

(R is a hydrogen atom, a lower alkyl group or a phenyl group), which process comprises adding a halide compound represented by the general formula (6)

(6)

(X is a halogen atom) to an unsaturated compound represented by the general formula (5)

(5)

(R has the same definition as given above) to form a trihalide compound represented by the general formula (1)

(1)

(X and R each have the same definition as given above), treating the trihalide compound with hydrogen halide (Y is a halogen atom) to form a trihalide compound represented by the general formula (2)

(2)

(X, Y and R each have the same definition as given above) and hydrolyzing the trihalide compound to obtain a compound represented by the general formula (4-O) shown above.

According to the present invention, there is also provided a process for producing an organogermanium compound represented by the general formula (4-O)

$$(Ge-\underset{\underset{R}{|}}{CH}-\underset{\underset{NH_2}{|}}{CH}-COOH)_2O_3 \quad (4\text{-}O)$$

(R is a hydrogen atom, a lower alkyl group or a phenyl group), which process comprises adding a halide compound represented by the general formula (6)

$$HGeX_3 \quad (6)$$

(X is a halogen atom) to an unsaturated compound represented by the general formula (5)

$$CH=\underset{\underset{R}{|}}{C}-COOH \quad (5)$$
$$\phantom{CH=}\underset{NHCOCH_3}{|}$$

(R has the same definition as given above) to form a trihalide compound represented by the general formula (1)

$$X_3Ge-\underset{\underset{R}{|}}{CH}-\underset{\underset{NHCOCH_3}{|}}{CH}-COOH \quad (1)$$

(X and R each have the same definition as given above), hydrolyzing the trihalide compound to obtain a sesquioxide compound represented by the general formula (3-O)

$$(Ge-\underset{\underset{R}{|}}{CH}-\underset{\underset{NHCOCH_3}{|}}{CH}-COOH)_2O_3 \quad (3\text{-}O)$$

(R has the same definition as given above), treating the sesquioxide compound with hydrogen halide
ti HY (Y is a halogen atom) to form a trihalide compound represented by the general formula (2)

$$X_3Ge-\underset{\underset{R}{|}}{CH}-\underset{\underset{NH_2.HY}{|}}{CH}-COOH \quad (2)$$

(X, Y and R each have the same definition as given above) and hydrolyzing the trihalide compound to obtain a compound represented by the general formula (4-O) shown above.

According to the present invention, there is also provided a process for producing an organogermanium compound represented by the general formula (4-S)

$$(Ge-\underset{\underset{R}{|}}{CH}-\underset{\underset{NH_2}{|}}{CH}-COOH)_2S_3 \quad (4\text{-}S)$$

(R is a hydrogen atom, a lower alkyl group or a phenyl group), which process comprises adding a halide compound represented by the general formula (6)

$$HGeX_3 \quad (6)$$

(X is a halogen atom) to an unsaturated compound represented by the general formula (5)

$$CH=\underset{\underset{R}{|}}{C}-COOH \quad (5)$$
$$\phantom{CH=}\underset{NHCOCH_3}{|}$$

(R has the same definition as given above) to form a trihalide compound represented by the general formula (1)

$$X_3Ge-\underset{\underset{R}{|}}{CH}-\underset{\underset{NHCOCH_3}{|}}{CH}-COOH \quad (1)$$

(X and R each have the same definition as given above), treating the trihalide compound with a hydrogen halide

HY (Y is a halogen atom) to form a trihalide compound represented by the general formula (2)

$$X_3Ge-\underset{\underset{R}{|}}{CH}-\underset{\underset{NH_2.HY}{|}}{CH}-COOH \quad (2)$$

(X, Y and R each have the same definition as given above) and reacting the trihalide compound with hydrogen sulfide $$H_2S$$

to obtain a compound represented by the general formula (4-S) shown above.

According to the present invention, there is also provided a process for producing an organogermanium compound represented by the general formula (3-S)

$$(Ge-\underset{\underset{R}{|}}{CH}-\underset{\underset{NHCOCH_3}{|}}{CH}-COOH)_2S_3 \quad (3\text{-}S)$$

(R is a hydrogen atom, a lower alkyl group or a phenyl group), which process comprises treating sesquioxide compound represented by the general formula (3-O)

$$(Ge-\underset{\underset{R}{|}}{CH}-\underset{\underset{NHCOCH_3}{|}}{CH}-COOH)_2O_3 \quad (3\text{-}O)$$

(R has the same definition as given above) with hydrogen sulfide $H_2S$ to obtain a compound represented by the general formula (3-S) shows above.

According to the present invention, there is also provide a process for producing an organogermanium compound represented by the general formula (4-S)

$$(Ge-\underset{\underset{R}{|}}{CH}-\underset{\underset{NH_2}{|}}{CH}-COOH)_2S_3 \quad (4\text{-}S)$$

(R is a hydrogen atom, a lower alkyl group or a phenyl group), which process comprises treating sesquioxide compound represented by the general formula (4-O)

(4-O)

(R has the same definition as given above) with hydrogen sulfide to obtained a compound represented by the general formula (4-S) shows above.

DETAILED DESCRIPTION OF THE INVENTION

The present invention is hereinafter described in detail.

In the organogermanium compound represented by the general formula (1) according to the present invention (1)

(X is a halogen atom and R is a hydrogen atom, a lower alkyl group or a phenyl group), the basic structure is a propionic acid derivative of germanium; three substituents X bond to the germanium atom; an acetyl-protected amino group bonds to the α-position carbon of the propionic acid structure; and a substituent R bonds to the β-position carbon of the propionic acid structure.

Since the X and the R in the above formula have the above definitions, the compound (1) includes the following specific compounds.

(1-a)

(1-b)

The organogermanium compound represented by the general formuls (2)

(2)

(X and Y are each a halogen atom and R is a hydrogen atom, a lower alkyl group or a phenyl group) according to the present invention is identical with the compound (1) except that —NH$_2$COCH$_3$ in the compound (1) is changed to —NH$_2$.HY in the compound (2). Accordingly, the compound (2) includes the following specific compounds.

(2-a)

(2-b)

The compounds (1) and (2) are particularly useful as intermediates for production of compounds (3) and (4) which are described below.

The organogermanium compound represented by the general formula (3-O)

(3-O)

(R is a hydrogen atom, a lower alkyl group or a phenyl group) according to the present invention is basically identical with the compounds (1) and (2) except that in the compound (3-O) a propionic acid derivative of germanium and oxygen atom bond to each other at a 2:3 ratio. Since in the compound (3-O) an acetyl-protected amino group bonds to the α-position carbon of the propionic acid structure, a substituent R bonds to the β-position carbon of the propionic acid structure, and the R has the same definition as given above, the compound (3-O) includes the following specific compounds.

(3-O-a)

(3-O-b)

The organogermanium compound represented by the general formula (3-S)

(3-S)

(R is a hydrogen atom, a lower alkyl group or a phenyl group) according to the present invention is different from the compound (3-O) in that in the compound (3-S) a propionic acid derivative of germanium and sulfur atom bond to each other at a 2:3 ratio. The compound (3-S) includes the following specific compounds.

(3-S-a)

(3-S-b)

The organogermanium compound represented by the general formula (4-O)

(4-O)

(R is a hydrogen atom, a lower alkyl group or a phenyl group) and the organogermanium compound represented by the general formula (4-S)

(4-S)

(R is a hydrogen atom, a lower alkyl group or a phenyl group) both according to the present invention corre- spond to modifications of the compound (3-O) and the compound (3-S), wherein the acetyl group present in the compounds (3-O) and (3-S) as an amino-protecting group is removed.

That is, the compounds (4-O) and (4-S) can be viewed as compounds wherein the basic structure is a propionic acid derivative of germanium, an amino group bonds to the α-position carbon of the propionic acid structure, a substituent R bonds to the β-position carbon of the propionic acid structure, and the basic structure and oxygen or sulfur atom bond to each other at a 2:3 ratio. Therefore, they can be viewed as compounds wherein an amino acid structure is introduced into carboxyethylgermanium sesquioxide or carboxyethylgermanium sesquisulfide.

Since the R in the compounds (4-O) and (4-S) has the above definition, the compounds (4-O) and (4-S) include the following specific compounds.

(4-O-a)

(4-O-b)

(4-S-a)

(4-S-b)

Carboxy group of each of above compounds is easily converted into its metallic salt by treating with base such as sodium hydroxide.

The compounds (4-O) and (4-S) are novel structure compounds and accordingly are highly expected to find novel utility.

In order to confirm the usefulness of the compounds (4-O) and (4-S) of the present invention, the following tests were conducted.

The compounds (4-O) and (4-S) were examined for oxidation-resistant property because some of organogermanium compounds show an oxidation-resistant property (Japanese Patent Publication No. 18590/1987). As a result, the compounds (4-O) and (4-S) of the present invention showed an oxidation-resistant property in a serum-present system which is a model of the inside of living body, as well as in a ion radical-present system which is a purely physicochemical system.

Further, the compounds (4-O) and (4-S) were examined for effects on Amadori rearrangement product which is a glucose-protein linkage product and which is drawing attention recently.

Glucose in living body had been known merely as an energy source. Recently, however, glucose came to be further viewed to have such activities as to bond to proteins and thereby to incur diabetes and other diseases resulting in acceleration of aging.

This reaction of glucose with proteins is called Maillard reaction or browning. In this reaction, an aldehyde group and an amino group bond to each other to form a Schiff base which is unstable, and the Schiff base quickly gives rise to an intramolecular hydrogen rearrangement reaction to change to an Amadori rearrangement product which is relatively stable. This product causes dehydration with the lapse of time to change to a glucose derivative. This derivative irreversibly bonds to other various molecules to produce AGE's (advanced glucosylation end products) which are yellowish brown fluorescent materials

It is believed that the AGE's form linkages with neighboring proteins incurring the sclerosis and/or aging of tissues. Specifically, hemoglobin $A_{IC}$ in diabetes is an Amadori rearrangement product; cataract is caused by a crystalline Amadori rearrangement product constituting the eye lens, that is, the Amadori rearrangement product causes further rearrangement to become an AGE and this AGE makes the lens cloudy. One of the compounds (4-O) and (4-S) was added to an experimentally prepared Amadori product formation system, where the compound significantly suppressed the formation of Amadori product.

The above described organogermanium compounds of the present invention can be produced according to the processes of the present invention as described below.

In one process of the present invention, firstly a halide compound represented by the general formula (6)

(X is a halogen atom) is added to an unsaturated compound represented by the general formula (5)

(5)

(R is a hydrogen atom, a lower alkyl group or a phenyl group) to form a compound of the present invention represented by the general formula (1)

(1)

(X and R each have the same definition as given above). This reaction proceeds in an organic solvent (e.g. ethyl ether) or an inorganic solvent (e.g. hydrochloric acid).

The above compound (1) is hydrolyzed to obtain a compound of the present invention represented by the general formula (3-O)

(3-O)

R has the same definition as given above).

The above hydrolysis reaction can be effected by any of conventional methods.

In other process of the present invention, the compound (1) is reacted with hydrogen sulfide $H_2S$ to obtain a compound of the present invention represented by the general formula (3-S)

(3-S)

(R is a hydrogen atom, a lower alkyl group or a phenyl group).

The above reaction can be easily effected, for example, by dissolving the compound (1) in an appropriate solvent and blowing thereinto H₂S gas.

In still other process of the present invention, the compound (1) is treated with a hydrogen halide HY (Y is a halogen atom) to form a compound of the present invention represented by the general formula (2)

(2)

(X and Y are each a halogen atom and R is a hydrogen atom, a lower alkyl group or a phenyl group). This reaction can be effected by treating the compound (1) with an aqueous hydrogen halide solution (e.g. hydrochloric acid), or by dissolving the compound (1) in water and blowing thereinto a hydrogen halide gas (e.g. hydrogen chloride gas).

The compound (2) is hydrolyzed to obtain a compound of the present invention represented by the general formula (4-O)

(4-O)

(R has the same definition as given above).

In still other process of the present invention, the compound (1) is hydrolyzed to form a compound (3-O) of the present invention (3-O)

(R is a hydrogen atom, a lower alkyl group or a phenyl group). The compound (3) is treated with a hydrogen halide HY (Y is a halogen atom) to form a hydrogen halide salt of the present invention represented by the general formula (2)

(2)

(X is a halogen atom, and Y and R each have the same definition as given above). The salt (2) is hydrolyzed to obtain a compound of the present invention represented by the general formula (4-O)

(4-O)

(R has the same definition as given above).

In still other process of the present invention, the salt (2) is reacted with hydrogen sulfide H₂S to obtain a compound of the present invention represented by the general formula (4-S)

(4-S)

(R is a hydrogen atom, a lower alkyl group or a phenyl group).

Further, an organogermanium compound represented by the general formula (3-S)

(3-S)

(R is a hydrogen atom, a lower alkyl group or a phenyl group), and represented by the general formula (4-S)

(4-S)

(R is a hydrogen atom, a lower alkyl group or a phenyl group) are obtained by treating sesquioxide compound represented by the general formula (3-O)

(3-O)

(R has the same definition as given above) and by the general formula (4-O), (4-O)

(R has the same definition as given above), with hydrogen sulfide

H₂S respectively.

The above reaction can be easily effected, as mentioned above, by dissolving compounds (3-O) and (4-O) in an appropriate solvent, such as water, and blowing thereinto H₂S gas.

Organogermanium compounds represented by the general formulas (3-O) and (4-O) dissociate into and in an aqueous solution, and hydroxy group —OH in above structures is converted into mercapto group —SH by the reaction with hydrogen sulfide, followed by intramolecular de-hydrogen sulfide reaction, and an organogermanium compounds represented by the general formulas (3-S) and (4-S) are obtained.

Incidentally, all of the above processes can be applied to the production of organogermanium compounds represented by the following formula.

BRIEF DESCRIPTION OF THE DRAWINGS

Incidentally, the values in FIG. 3 represent the contents of organogermanium compound used, in terms of mg/ml.

DESCRIPTION OF EXAMPLES

The present invention is described in detail below by way of Examples.

Example 1

Synthesis of compound (1-a)

12.90 g (0.10 mol) of 2-acetoaminoacrylic acid was suspended in 300 ml of ethyl ether. To the suspension was slowly added 21.61 g (0.12 mol) of trichlorogermane at room temperature, whereby the suspension became a solution.

The solution was stirred for 1 hour at room temperature. The resulting insoluble matters were removed by filtration. The filtrate was subjected to distillation to remove the solvent and thereby to obtain 29.40 g (yield: 95.1%) of a colorless transparent gum-like compound. Upon drying under reduced pressure, the gum-like compound became a hygroscopic crystalline powder having a melting point of 103°–104° C.

Elemental analysis (% by weight) Calculated; C 19.43, H 2.61, Ge 23.49, N 4.53, Cl 34.41
Found: C 19.52, H 2.65, Ge 23.52, N 4.61, Cl 34.44.
IR $\nu$ KBr/max cm$^{-1}$: 1720, 1625 (C=O)
$^1$H-NMR (CD$_3$OD) $\delta$: 2.00 (3H, s, —C$\underline{H}_3$), 2.34, 2.55 (2H, dd, Ge-C$\underline{H}_2$),
4.76 (1H, brt, C$\underline{H}$—CO)

Example 2

Synthesis of compound (2-a)

15.46 g (0.05 mol) of the compound (1-a) obtained in Example 1 was placed in 150 ml of concentrated hydrochloric acid. The mixture was refluxed for 2 hours. After cooling, the mixture was concentrated to dryness under reduced pressure to remove hydrochloric acid and thereby to obtain 15.10 g (yield: 99.5%) of a white crystal. The crystal decomposed at a temperature of 250° C. or higher.

Elemental analysis (% by weight) Calculated: C 11.87, H 2.32, Ge 23.92, N 4.62, Cl 46.73 Found: C 11.91, H 2.35, Ge 23.85, N 4.58, Cl 46.71.
IR $\nu$ KBr/max cm$^{-1}$: 1720 (C=O), 425, 410 (Ge-Cl)
$^1$H-NMR (CDCl$_3$+CD$_3$OD) $\delta$:2.71 (2H, brd, Ge-C$\underline{H}_2$) 4.45 (1H, brt, CH—CO)

Example 3 Synthesis of compound (3-O-a)

2.68 g (0.01 mol) of the compound (1-a) obtained in Example 1 was placed in 200 ml of water. The mixture was stirred for 1 hour at room temperature and then filtered. The filtrate was passed through a cation exchange resin. Then, 500 ml of water was passed through the resin. The resulting solution was concentrated to dryness to obtain 1.85 g (yield: 81.6%) of a white crystal. The crystal decomposed at a temperature of 270° C. or higher.

Elemental analysis (% by weight) Calculated: C 26.49, H 3.55, Ge 32.02, N 6.18; Found: C 26.51, H 3.51, Ge 32.00, N 6.22.
IR $\nu$ Kbr/max cm$^{-1}$; 1720, 1640 (C=O), 870 (Ge-O)
$^1$H-NMR (D$_2$O) $\delta$: 2.01 (2H, d, Ge-C$\underline{H}_2$), 2.04 (3H, s, C$\underline{H}_3$). 4.64 (1H, t, —C$\underline{H}$—CO)

The compound (3-O-a) was treated with, for example, concentrated hydrochloric acid to obtain a compound. The compound agreed completely with the compound (2-a) obtained in Example 2.

Example 4

Synthesis of compound (4-O-a)

3.04 g (0.01 mol) of the compound (2-a) obtained in Example 2 was dissolved in 100 ml of water and adsorbed by a cation exchange resin. Then, 500 ml of. 2 N NH$_4$OH was passed through the resin to elute the compound. The eluate was concentrated to dryness to obtain 1.80 g (yield: 97.5%) of a white crystal. The crystal decomposed at a temperature of 270° C. or higher.

Elemental analysis (% by weight) Calculated: C 19.51, H 3.27, Ge 39.31, N 7.59 Found: C 19.44, H 3.19, Ge 39.40, N 7.61
IR $\nu$ KBr/max cm$^{-1}$: 1670 (C=O) 880, 810 (Ge-O)
$^1$H-NMR (D$_2$O) $\nu$: 1.95 (2H, brd, Ge-C$\underline{H}_2$), 4.12 (1H, brt, —C$\underline{H}$—CO)

Example 5

Synthesis of compound (3-S-a)

23.81 g (77 mmol) of the compound (1-a) obtained in Example 1 was dissolved in 50 ml of hot water. Hydrogen sulfide (H$_2$S) gas was bubbled in the solution. The resulting crystal was collected by filtration and dried to obtain 15.5 g (yield: 80.27%) of a light yellow crystalline powder. The crystal decomposed at a temperature of 300° C. or higher.

Elemental analysis (% by weight)
Calculated: C 23.94, H 3.22, N 5.58 Found: C 24.20, H 3.41, N 5.26
$^1$H-NMR (D$_2$O+NaOD) $\delta$: 1.50 (2H, m, Ge-C$\underline{H}_2$) 2.03 (3H, s, C$\underline{H}_3$) 4.23 (1H, m,—C$\underline{H}$—CO)

Example 6

Synthesis of compound (4-S-a)

5.00 g (16.5 mmol) of the compound (2-a) obtained in Example 2 was dissolved in 25 ml of hot water with the addition of 2.6 g (66 mmol) of sodium hydroxide. Hydrogen sulfide gas was bubbled in the solution with stirring. The resulting crystal was collected by filtration and dried to obtain 1.2 g (yield: 35.3%) of the title compound. The compound was a colorless hygroscopic crystal having a melting point of 300° C. or higher.

Elemental analysis (% by weight) Calculated: C 17.26, H 2.90, N 6.71 Found; C 17.10, H 3.23, N 6.74
IR $\nu$KBr/max cm$^{-1}$: 1630 (C=O), 410 (Ge-S)
$^1$H-NMR (D2O) $\delta$: 1.50 (2H, m, Ge-C$\underline{H}_2$), 3.53 (1H, m, —C$\underline{H}$—CO)

Example 7

Synthesis of compound (1-b)

20.51 g (0.10 mol) of 2-acetoaminocinnamic acid was suspended in 300 ml of concentrated hydrochloric acid.

Thereto was added 21.61 g (0.12 mol) of trichlorogermane at room temperature. The mixture was stirred with heating.

After cooling, a crystal precipitated. It was collected by filtration and dried to obtain 35.30 g (yield: 91.7%) of a white crystal. The crystal decomposed at a temperature of 300° C.

Elemental analysis (% by weight) Calculated: C 34.30, H 3.14, Ge 18.85, N 3.64, Cl 27.61 Found: C 34.27, H 3.19, Ge 18.80, N 3.68, Cl 27.56

IR $\nu$ KBr/max cm$^{-1}$: 1735 (C=O), 1630 (N—C=O), 420 (Ge—Cl)

$^1$H—NMR (CDCl$_3$+CD$_3$OD) δ; 1.97 (3H, s, —CH$_3$), 4.10 (1H, d, Ge—CH), 5.33 (1H, d, CH—CO), 7.30 (5H, brs, —C$_6$H$_5$)

Example 8

Synthesis of compound (2-b)

3.85 g (0.10 mol) of the compound (1-b) obtained in Example 7 was dissolved in 350 ml of water. Hydrogen chloride gas was bubbled in the solution. After cooling, a crystal precipitated. The crystal was collected by filtyration and dried under reduced pressure to obtain 23.10 g (yield: 60.9%) of a white crystal. The crystal decomposed at a temperature of 300° C. or higher.

Elemental analysis (% by. weight) Calculated: C 28.48, H 2.92, Ge 19.12, N 3.69, Cl 37.36 Found: C 28.44, H 2.96, Ge 19.06, N 2.96, Cl 37.07.

IR $\nu$ KBr/max cm$^{-1}$: 1755 (C=), 430, 410 (Ge—Cl)

$^1$H—NMR (CD$_3$OD) δ: 4.25 (1H, d, Ge—CH), 4.82 (1H, d, CH—CO), 7.40 (5H, s, C$_6$H$_5$)

Example 9

Synthesis of compound (3-O-b)

3.85 g (0.01 mol) of the compound (1-b) obtained in Example 7 was placed in 200 ml of water. The mixture was stirred for 1 hour at room temperature and then passed through a cation exchange resin. Thereafter, 300 ml of water was passed through the resin. The resulting solution was concentrated to dryness to obtain 2.42 g (yield: 80.0%) of a white crystal. The crystal decomposed at a temperature of 250° C. or higher.

Elemental analysis (% by weight) Calculated: C 43.63, H 3.99, Ge 23.97, N 4.63 Found C 43.50, H 3.96, Ge 23.87, N 4.70.

IR $\nu$ KBr/max cm$^{-1}$: 1 1710, 1650 (C=O), 880 (Ge-O)

$^1$H-NMR (D$_2$O) δ: 1.83 (3H, s, CH$_3$), 3.48 (1H, brd, Ge—CH), 4.92 (1H, brd, —CH—CO), 6.97-7.50 (5H, br, —C$_6$H$_5$)

The compound (3-O-b) was treated with concentrated hydrochloric acid to obtain a compound. The compound agreed completely with the compound (2-b) obtained in Example 6.

Example 10

Synthesis of compound (4-O-b)

11.40 g (0.03 mol) of the compound (2-b) obtained in Example 8 was dissolved in 400 ml of water and adsorbed by a cation exchange resin. The compound on the resin was eluted by 300 ml of 2N NH$_4$O H and the eluate was concentrated to dryness to obtain 7.20 g (Yield: 92.1%) of a white crystal. The crystal decomposed at a temperature of 300° C. or higher.

Elemental analysis (% by weight) Calculated: C 41.45, H 3.87, Ge 27.84, N 5.37 Found C 41.38, H 3.88, Ge 27.80, N 5.40

IR $\nu$ KBr/max cm$^{-1}$: 1 1640 (C=O) 850 (Ge-O)

$^1$H-NMR (D$_2$O) δ: 3.45 (1H, d, Ge—CH) 4.39 (1H, d, —CH—CO) 7.35 (5H, m, —C$_5$H$_5$)

Example 11

Synthesis of compound (3-S-b)

3.18 g (8 mmol) of the compound (1-b) obtained in Example 7 was dissolved in 50 ml of hot water. Hydrogen sulfide gas was bubbled in the solution. The resulting crystal was collected by filtration and dried to obtain 2.15 g (yield: 82.22%) of the title compound. The compound was a colorless crystal having a melting point of 300° C. or higher.

Elemental analysis (% by weight) Calculated: C 40.42, H 3.70, N 4.23 Found: C 40.68, H 3.66, N 4.40.

IR $\nu$ KBr/max cm$^{-1}$: 1720 (C=O), 1650 (C=O), 420 (Ge-S)

$^1$H—NMR (D$_2$O+1% NaOD) δ: 2.03 (3H, s, CH$_3$), 3.03 (2H, m, CO—CH—NH),

Example 12

Synthesis of compound (4-S-b)

10.00 g (26 mmol) of the compound (2-b) obtained in Example 8 was dissolved in 30 ml of hot water with the addition of 4.2 g (0.11 mmol) of sodium hydroxide. The solution was stirred. Hydrogen sulfide gas was bubbled in the solution. The resulting crystal was collected by filtration and dried to obtain 2.68 g (yield: 35.7%) of the title compound. The compound was a colorless crystal having a melting point of 300° C. or higher.

Elemental analysis (% by weight) Calculated: C 37.95, H 3.54, N 4.92 Found: C 38.12, H 3.67, N 4.59.

IR $\nu$ KBr/max cm$^{-1}$: 1630 (C=O)

$^1$H—NMR (D$_2$O+NaOD) δ: 2.90 (1H, d, —CH—CO), 3.90 (1H, d, —CH—Ge), 7.30 (5H, m, —Ph)

Test 1 Oxidation-resistant property of compound (4O-a)

The following solutions were prepared.

| Test 1 Oxidation-resistant property of compound (4-O-a) The following solutions were prepared. | |
|---|---|
| (1) 0.1 M citric acid-phosphoric acid buffer solution (pH 5.0) | 1.5 ml |
| (2) O-Phenylenediamine (1 mg/ml) | 1.0 ml |
| (3) Serum | 2.0 ml |
| (4) Solution of compound (4-0-a) of the present invention | 0.1 ml |
| (5) 1% H$_2$O$_2$ solution | 0.2 ml |

(5) 1% H$_2$O$_2$ solution 0.2 ml

The components (1), (2), (3) and (4) were mixed and maintained at 37° C. for 2 hours, then the mixture was measured for absorbancy at 430 nm to evaluate the oxidation-resistant property of the compound (4O-a) in a serum-present system which is a model of the inside of living body.

Figure 1:
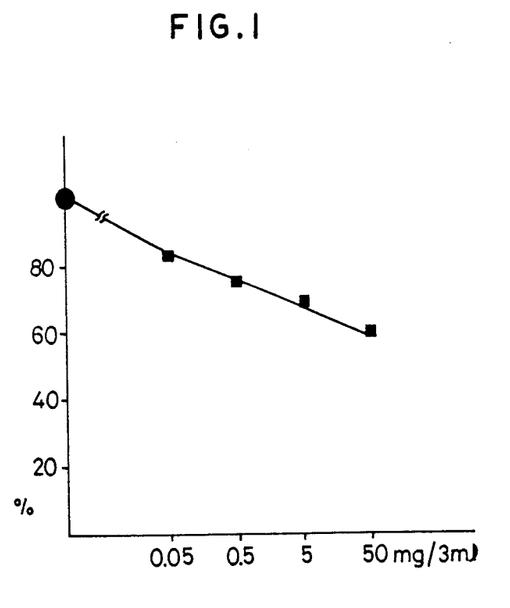
FIG. 1 is a graph showing that one of the organogermanium compounds of the present invention exhibits an oxidation-resistant property in a serum-present system which is a model of the inside of living body.
Figure 2:
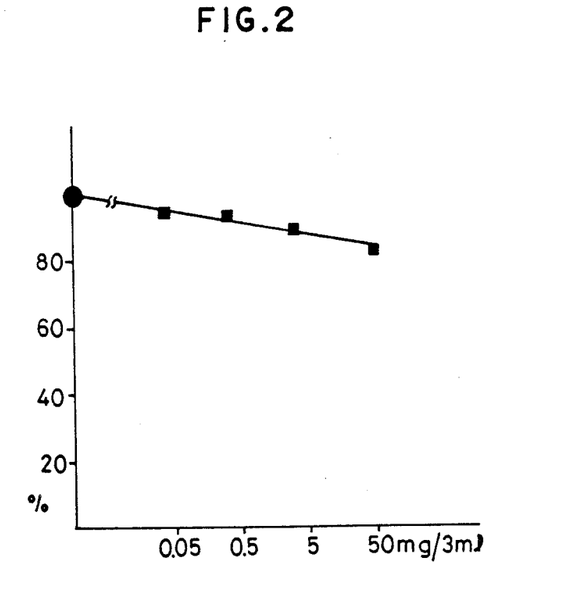
FIG. 2 is a graph showing that one of the organogermanium compound of the present invention exhibits an oxidation-resistant property in an ion radical-present system which is a purely physicochemical system.

Further, the components (1), (2), (4) and (5) were mixed and irradiated with an ultraviolet light for 2 hours, then the mixture was measured for absorbancy at 430 nm to evaluate the oxidation-resistant property of the compound (4O-a) in an ion radical-present system which is a purely physicochemical system The results are shown in FIG. 1 and FIG. 2, respectively. As is clear from FIGS. 1 and 2, the compound (4-O-a) of the present invention showed oxidation-resistant property in a serum-present system which is a model of the inside of living body, as well as in an ion radical-present system which is a purely physicochemical system.

Test 2 Suppression of Amadori rearrangement product formation,

| Test 2 Suppression of Amadori rearrangement product formation, by compound (4-O-a) | |
|---|---|
| (1) Bovine serum albumin in phosphoric acid buffer solution of pH 7.4 | 200 mg/ml |
| (2) D-glucose | 200 mM |
| (3) Sodium nitride | 3 mM |

To a mixture consisting of the above components (1), (2) and (3) was added a compound (4-O-a) of the present invention at various concentrations. Each of the resulting mixture was heated to 37° C. Each mixture was measured for fluorescence intensity by a fluorophotometer (excitation wave=370 nm, emission wave=440 nm), with the lapse of time.

Figure 3:
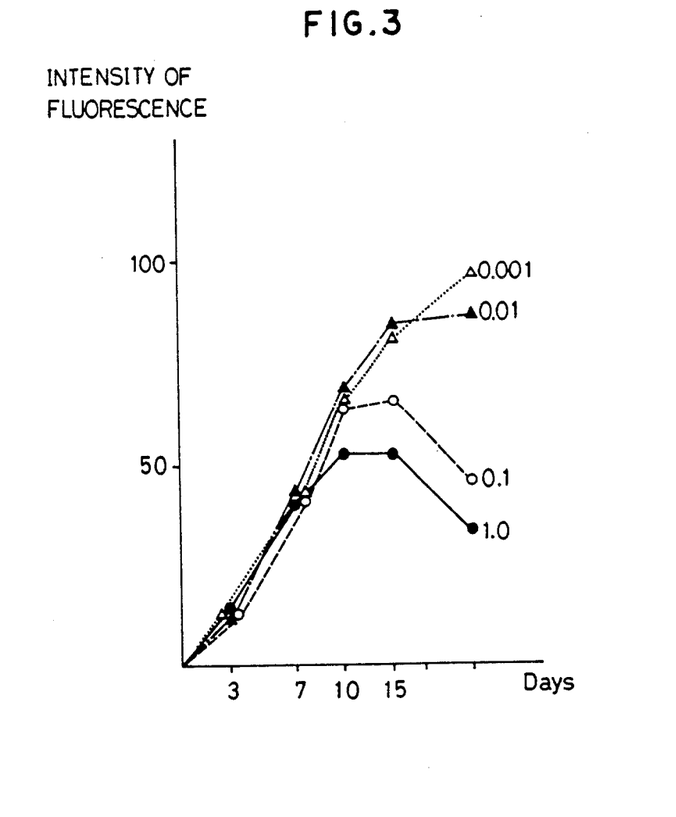
FIG. 3 is a graph showing that one of the organogermanium compounds of the present invention suppresses the formation of Amadori rearrangement product.

The results are shown in FIG. 3. As is clear from FIG. 3, the once formed AGE gradually decreased its fluorescence intensity, that is, the presence of the organogermanium compound (4-O-a) of the present invention caused the structural change of the AGE.

Results similar to those in Tests 1 and 2 were seen also with the compounds (4-O-b) and (4-S) of the present invention.

What is claimed is:

1. An organogermanium compound represented by the general formula (1)

$$X_3Ge-\underset{R}{CH}-\underset{NHCOCH_3}{CH}-COOH \qquad (1)$$

wherein X is a halogen atom and R is a hydrogen atom, a lower alkyl group or a phenyl group.

2. An organogermanium compound represented by the general formula (2)

$$X_3Ge-\underset{R}{CH}-\underset{NH_2 \cdot HY}{CH}-COOH \qquad (2)$$

wherein X and Y are each a halogen atom and R is a hydrogen atom, a lower alkyl group or a phenyl group.

3. An organogermanium compound represented by the general formula (3-O)

$$(Ge-\underset{R}{CH}-\underset{NHCOCH_3}{CH}-COOH)_2O_3 \qquad (3-O)$$

wherein R is a hydrogen atom, a lower alkyl group or a phenyl group.

4. An organogermanium compound represented by the general formula (3-S)

$$(Ge-\underset{R}{CH}-\underset{NHCOCH_3}{CH}-COOH)_2S_3 \qquad (3-S)$$

wherein R is a hydrogen atom, a lower alkyl group or a phenyl group.

5. An organogermanium compound represented by the general formula (4-O)

$$(Ge-\underset{R}{CH}-\underset{NH_2}{CH}-COOH)_2O_3 \qquad (4-O)$$

wherein R is a hydrogen atom, a lower alkyl group or a phenyl group.

6. An organogermanium compound represented by the general formula (4-S)

$$(Ge-\underset{R}{CH}-\underset{NH_2}{CH}-COOH)_2S_3 \qquad (4-S)$$

wherein R is a hydrogen atom, a lower alkyl group or a phenyl group.

7. A process for producing an organogermanium compound represented by the general formula (3-O)

$$(Ge-\underset{R}{CH}-\underset{NHCOCH_3}{CH}-COOH)_2O_3 \qquad (3-O)$$

(R is a hydrogen atom, a lower alkyl group or a phenyl group), which process comprises adding a halide compound represented by the general formula (6)

$$HGeX_3 \qquad (6)$$

(X is a halogen atom) to an unsaturated compound represented by the general formula (5)

$$\underset{R}{CH}=\underset{NHCOCH_3}{C}-COOH \qquad (5)$$

(R has the same definition as given above) to form a trihalide compound represented by the general formula (1)

$$X_3Ge-\underset{R}{CH}-\underset{NHCOCH_3}{CH}-COOH \qquad (1)$$

(X and R each have the same definition as given above) and hydrolyzing the trihalide compound to obtain a compound represented by the general formula (3-O) shown above.

8. A process for producing an organogermanium compound represented by the general formula (3-S)

$$(Ge-\underset{R}{CH}-\underset{NHCOCH_3}{CH}-COOH)_2S_3 \qquad (3-S)$$

(R is a hydrogen atom, a lower alkyl group or a phenyl group), which process comprises adding a halide compound represented by the general formula (6)

$$HGeX_3 \qquad (6)$$

(X is a halogen atom) to an unsaturated compound represented by the general formula (5)

$$\underset{R}{CH}=\underset{NHCOCH_3}{C}-COOH \qquad (5)$$

(R has the same definition as given above) to form a trihalide compound represented by the general formula (1)

$$X_3Ge-\underset{R}{CH}-\underset{NHCOCH_3}{CH}-COOH \quad (1)$$

(X and R each have the same definition as given above) and reacting the trihalide compound with hydrogen sulfide $$H_2S$$

to obtain a compound represented by the general formula (3-S) shown above.

9. A process for producing an organogermanium compound represented by the general formula (4-O)

$$(Ge-\underset{R}{CH}-\underset{NH_2}{CH}-COOH)_2O_3 \quad (4\text{-}O)$$

(R is a hydrogen atom, a lower alkyl group or a phenyl group), which process comprises adding a halide compound represented by the general formula (6)

$$HGeX_3 \quad (6)$$

(X is a halogen atom) to an unsaturated compound represented by the general formula (5)

$$\underset{R}{CH}=\underset{NHCOCH_3}{C}-COOH \quad (5)$$

(R has the same definition as given above) to form a trihalide compound represented by the general formula (1)

$$X_3Ge-\underset{R}{CH}-\underset{NHCOCH_3}{CH}-COOH \quad (1)$$

(X and R each have the same definition as given above), treating the trihalide compound with hydrogen halide $$HY$$

(Y is a halogen atom) to form a trihalide compound represented by the general formula (2)

$$X_3Ge-\underset{R}{CH}-\underset{NH_2.HY}{CH}-COOH \quad (2)$$

(X, Y and R each have the same definition as given above) and hydrolyzing the trihalide compound to obtain a compound represented by the general formula (4-O) shown above.

10. A process for producing an organogermanium compound represented by the general formula (4-O)

$$(Ge-\underset{R}{CH}-\underset{NH_2}{CH}-COOH)_2O_3 \quad (4\text{-}O)$$

(R is a hydrogen atom, a lower alkyl group or a phenyl group), which process comprises adding a halide compound represented by $$HGeX_3 \quad (6)$$

(X is a halogen atom) to an unsaturated compound represented by the general formula (5)

$$\underset{R}{CH}=\underset{NHCOCH_3}{C}-COOH \quad (5)$$

(R has the same definition as given above) to form a trihalide compound represented by the general formula (1)

$$X_3Ge-\underset{R}{CH}-\underset{NHCOCH_3}{CH}-COOH \quad (1)$$

(X and R each have the same definition as given above), hydrolyzing the trihalide compound to obtain a sesquioxide compound represented by the general formula (3-O)

$$(Ge-\underset{R}{CH}-\underset{NHCOCH_3}{CH}-COOH)_2O_3 \quad (3\text{-}O)$$

(R has the same definition as given above), treating the sesquioxide compound with hydrogen halide $$HY$$

(Y is a halogen atom) to form a trihalide compound represented by the general formula (2)

$$X_3Ge-\underset{R}{CH}-\underset{NH_2.HY}{CH}-COOH \quad (2)$$

(X, Y and R each have the same definition as given above) and hydrolyzing the trihalide compound to obtain a compound represented by the general formula (4-O) shown above.

11. A process for producing an organogermanium compound represented by the general formula (4-S)

$$(Ge-\underset{R}{CH}-\underset{NH_2}{CH}-COOH)_2S_3 \quad (4\text{-}S)$$

(R is a hydrogen atom, a lower alkyl group or a phenyl group), which process comprises adding a halide compound represented by the general formula (6)

$$HGeX_3 \quad (6)$$

(X is a halogen atom) to an unsaturated compound represented by the general formula (5)

$$\underset{R}{CH}=\underset{NHCOCH_3}{C}-COOH \quad (5)$$

(R has the same definition as given above) to form a trihalide compound represented by the general formula (1)

$$X_3Ge-\underset{R}{CH}-\underset{NHCOCH_3}{CH}-COOH \quad (1)$$

(X and R each have the same definition as given above), treating the trihalide compound with a hydrogen halide

HY (Y is a halogen atom) to form a trihalide compound represented by the general formula (2)

$$X_3Ge-\underset{R}{CH}-\underset{NH_2 \cdot HY}{CH}-COOH \quad (2)$$

(X, Y and R each have the same definition as given above) and reacting the trihalide compound with hydrogen sulfide

H₂S to obtain a compound represented by the general formula (4-S) shown above.

12. A process for producing an organogermanium compound represented by the general formula (3-S)

$$(Ge-\underset{R}{CH}-\underset{NHCOCH_3}{CH}-COOH)_2S_3 \quad (3-S)$$

(R is a hydrogen atom, a lower alkyl group or a phenyl group), which process comprises treating sesquioxide compound represented by the general formula (3-O)

$$(Ge-\underset{R}{CH}-\underset{NHCOCH_3}{CH}-COOH)_2O_3 \quad (3-O)$$

(R has the same definition as given above) with hydrogen sulfide

H₂S to obtain a compound represented by the general formula (3-S) shows above.

13. A process for producing an organogermanium compound represented by the general formula (4-S)

$$(Ge-\underset{R}{CH}-\underset{NH_2}{CH}-COOH)_2S_3 \quad (4-S)$$

(R is a hydrogen atom, a lower alkyl group or a phenyl group), which process comprises treating sesquioxide compound represented by the general formula (4-O)

$$(Ge-\underset{R}{CH}-\underset{NH_2}{CH}-COOH)_2O_3 \quad (4-O)$$

(R has the same definition as given above) with hydrogen sulfide

H₂S to obtain a compound represented by the general formula (3-S) shows above.

* * * * *